United States Patent [19]
Wan et al.

[11] Patent Number: 5,830,220
[45] Date of Patent: Nov. 3, 1998

[54] SUTURING INSTRUMENT

[76] Inventors: Shaw P. Wan, 603 Lariat La., Rolla, Mo. 65401; Rosendo Martinez, 790 Prigge Rd., St. Louis, Mo. 63138

[21] Appl. No.: 815,620

[22] Filed: Mar. 13, 1997

[51] Int. Cl.$^6$ .................................................. A61B 17/04
[52] U.S. Cl. ......................... 606/139; 606/148; 604/272; 128/898
[58] Field of Search .................... 606/139, 144, 606/147, 148; 604/272; 128/898

[56] References Cited

U.S. PATENT DOCUMENTS

| | | | |
|---|---|---|---|
| 43,098 | 6/1864 | Cooper . | |
| 4,172,458 | 10/1979 | Pereyra | 128/340 |
| 5,149,329 | 9/1992 | Richardson | 604/272 |
| 5,152,749 | 10/1992 | Giesy et al. | 604/164 |
| 5,167,645 | 12/1992 | Castillo | 604/272 |
| 5,282,809 | 2/1994 | Kammerer et al. | 606/148 |
| 5,336,230 | 8/1994 | Leichtling et al. | 606/148 |
| 5,342,374 | 8/1994 | Wan et al. | 606/148 |
| 5,423,836 | 6/1995 | Brown | 606/148 |
| 5,439,469 | 8/1995 | Heaven et al. | 606/144 |
| 5,468,251 | 11/1995 | Buelna | 606/223 |
| 5,480,405 | 1/1996 | Yoon | 606/143 |
| 5,480,407 | 1/1996 | Wan et al. | 606/148 |
| 5,520,703 | 5/1996 | Essig et al. | 606/148 |

FOREIGN PATENT DOCUMENTS 163715  7/1964  Russian Federation .
1309971A1  5/1987  Russian Federation .

OTHER PUBLICATIONS

Walsh et al. "Anatomical Radical Retropubic Prostatectomy: Evolution of the Surgical Technique", Brochure, pp. 1–15, Mar. 1993.

*Primary Examiner*—Gary Jackson
*Attorney, Agent, or Firm*—Senniger, Powers, Leavitt & Roedel

[57] ABSTRACT

An instrument comprising a substantially rigid guide tube having opposite open ends which are distal and proximal relative to a person using the instrument. The guide tube has a shank portion and a distal end portion extending generally laterally with respect to the shank portion. A handle is provided on the shank portion of the guide tube generally adjacent the proximal end of the guide tube. A stiff but flexible shaft inside the guide tube has a distal end part movable distally relative to the guide tube to extend through and beyond the open distal end of the guide tube. A suture thread holder is provided on the distal end part of the shaft. The shaft is manually movable relative to the guide tube to move the distal end part of the shaft and the suture thread holder from a retracted position to an extended position along a substantially straight path extending generally laterally at an angle of not substantially less than ninety degrees with respect to the shank portion of the guide tube.

18 Claims, 7 Drawing Sheets

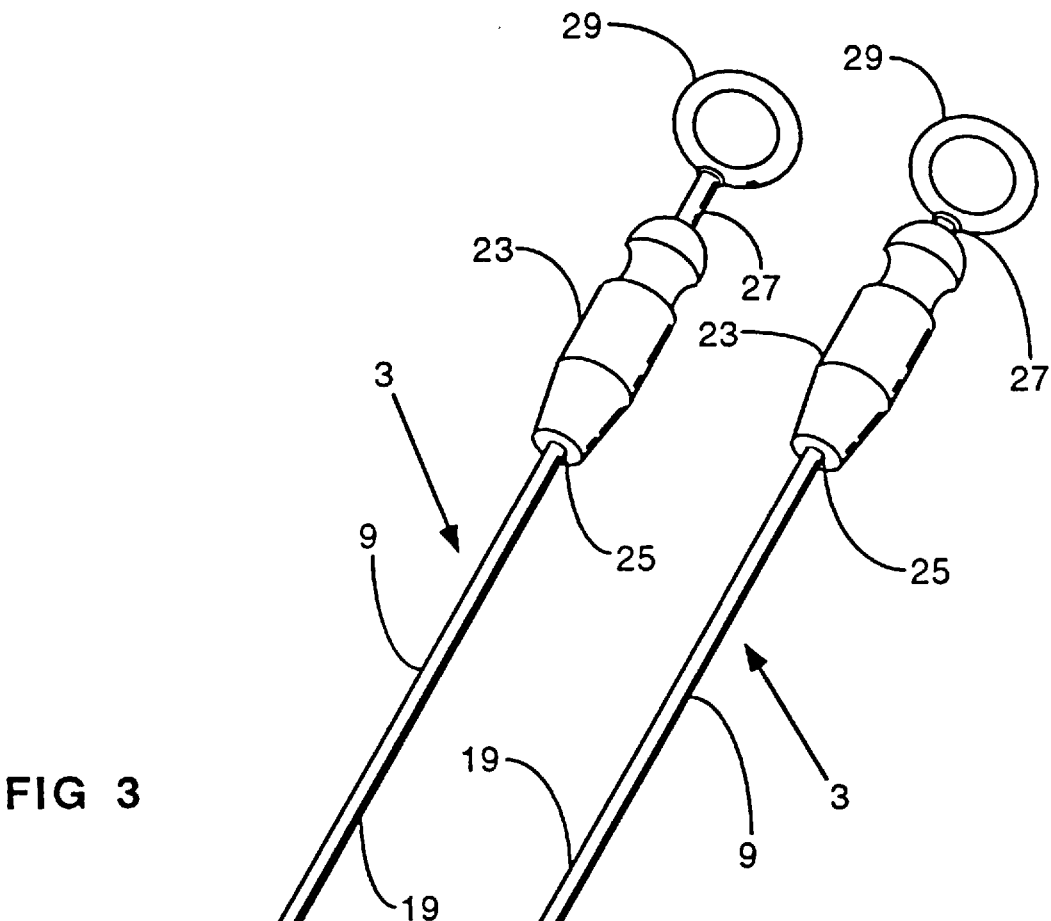
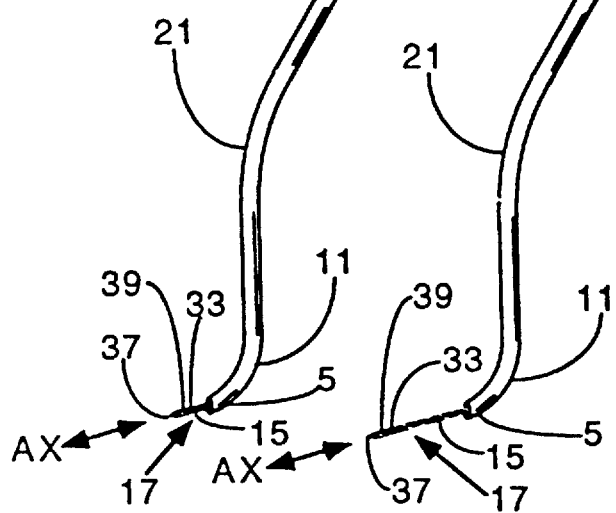
FIG 3
FIG 4

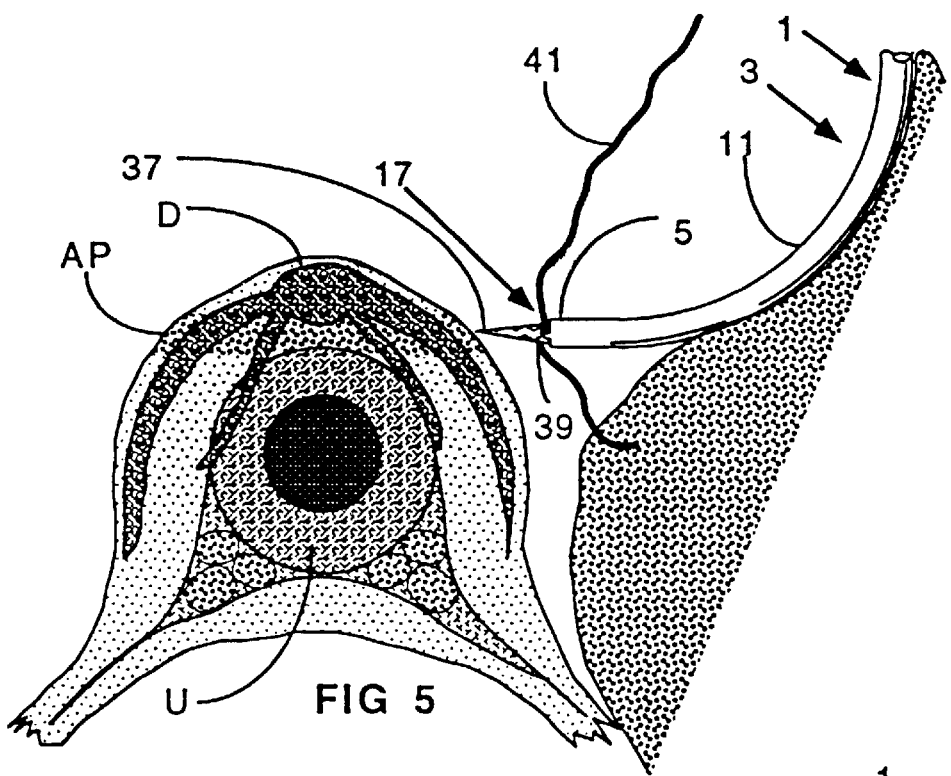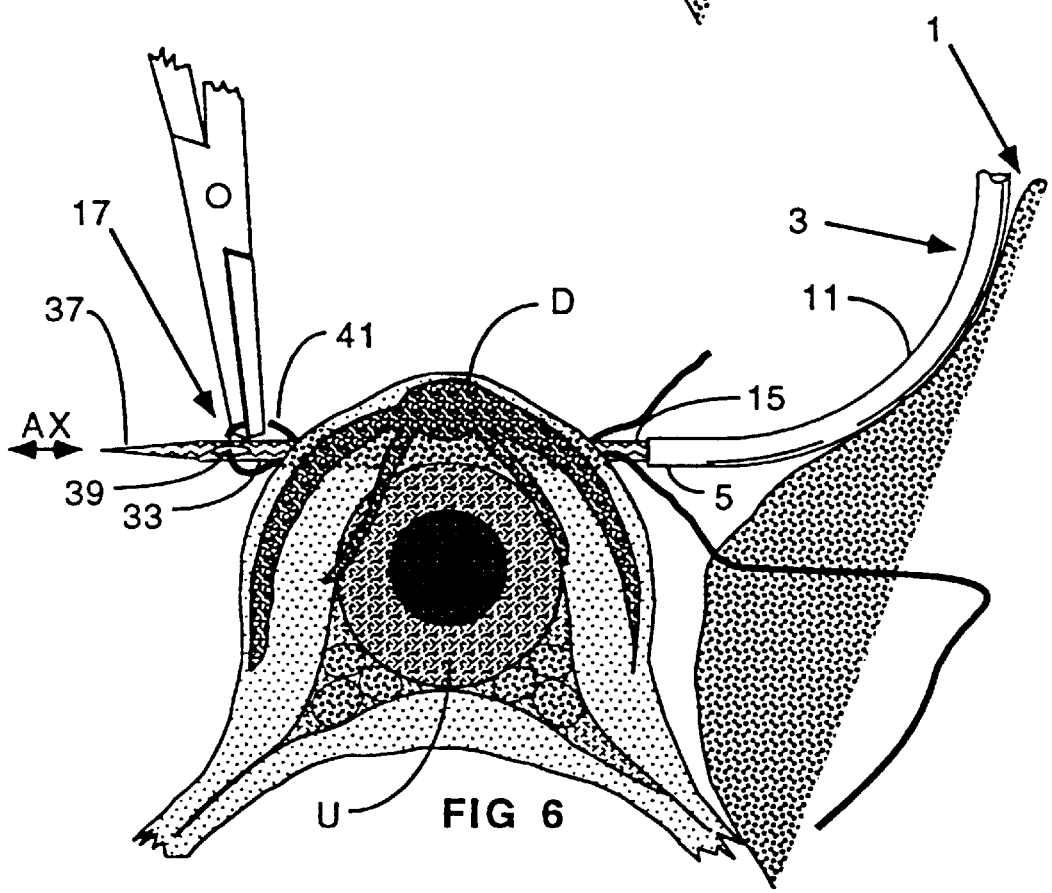

PREVIOUS ART

PREVIOUS ART

PREVIOUS ART

SUTURING INSTRUMENT

BACKGROUND OF THE INVENTION

The present invention relates to an instrument which can be used in a suturing procedure, especially a radical prostatectomy procedure.

Radical prostatectomy requires ligation of the dorsal vein complex. This is a difficult procedure because access to the dorsal vein complex, particularly its distal end, is inhibited by the close proximity of the pubic symphysis, pelvic wall, prostate and urethra. Surgeons have used various methods and instruments to suture the dorsal vein complex, but none have been entirely satisfactory.

Accordingly, there is a need for an instrument which facilitates suturing in tight areas which are difficult to access, and which is particularly useful in effecting the ligation of the dorsal vein complex, especially the distal end of the complex located under the pubic symphysis, before it is severed during a radical prostatectomy.

SUMMARY OF THE INVENTION

Among the several objects of this invention may be noted the provision of an instrument for use in a suturing procedure, especially a radial prostatectomy; the provision of such an instrument which facilitates ligation of the dorsal vein complex during such a procedure; the provision of such an instrument which is safe and easy to use, and which can be designed for either left-hand or right-hand use; and the provision of such an instrument which is simple in design for economical manufacture.

Briefly, an instrument of the present invention comprises a substantially rigid guide tube having opposite open ends which are distal and proximal relative to a person using the instrument. The guide tube has a shank portion and a distal end portion extending generally laterally with respect to the shank portion. A handle is provided on the shank portion of the guide tube generally adjacent the proximal end of the guide tube. A stiff but flexible shaft inside the guide tube has a distal end part movable distally relative to the guide tube to extend through and beyond the open distal end of the guide tube. A suture thread holder is provided on the distal end part of the shaft. The shaft is manually movable relative to the guide tube to move the distal end part of the shaft from a retracted position in which the suture thread holder is generally adjacent the open distal end of the guide tube, to an extended position in which the suture thread holder is farther away from the distal end of the guide tube and farther away from the shank portion of the guide tube. The distal end portion of the guide tube is configured to guide the distal end part of the shaft and the suture thread holder thereon along a substantially straight path extending generally laterally at an angle of not substantially less than ninety degrees with respect to the shank portion of the guide tube.

Other objects and features will be in part apparent and in part pointed out hereinafter.

BRIEF DESCRIPTION OF THE DRAWINGS

FIG. 3 is a view of the instrument of FIG. 1 showing a flexible shaft of the instrument in a retracted position;

FIG. 4 is a view similar to FIG. 3 showing the shaft in an extended position;

FIGS. 5–7 illustrate a method of using the instrument in a radical prostatectomy procedure.

Corresponding parts are designated by corresponding reference numerals throughout the several views of the drawings.

DETAILED DESCRIPTION OF THE PREFERRED EMBODIMENT

Figure 1:
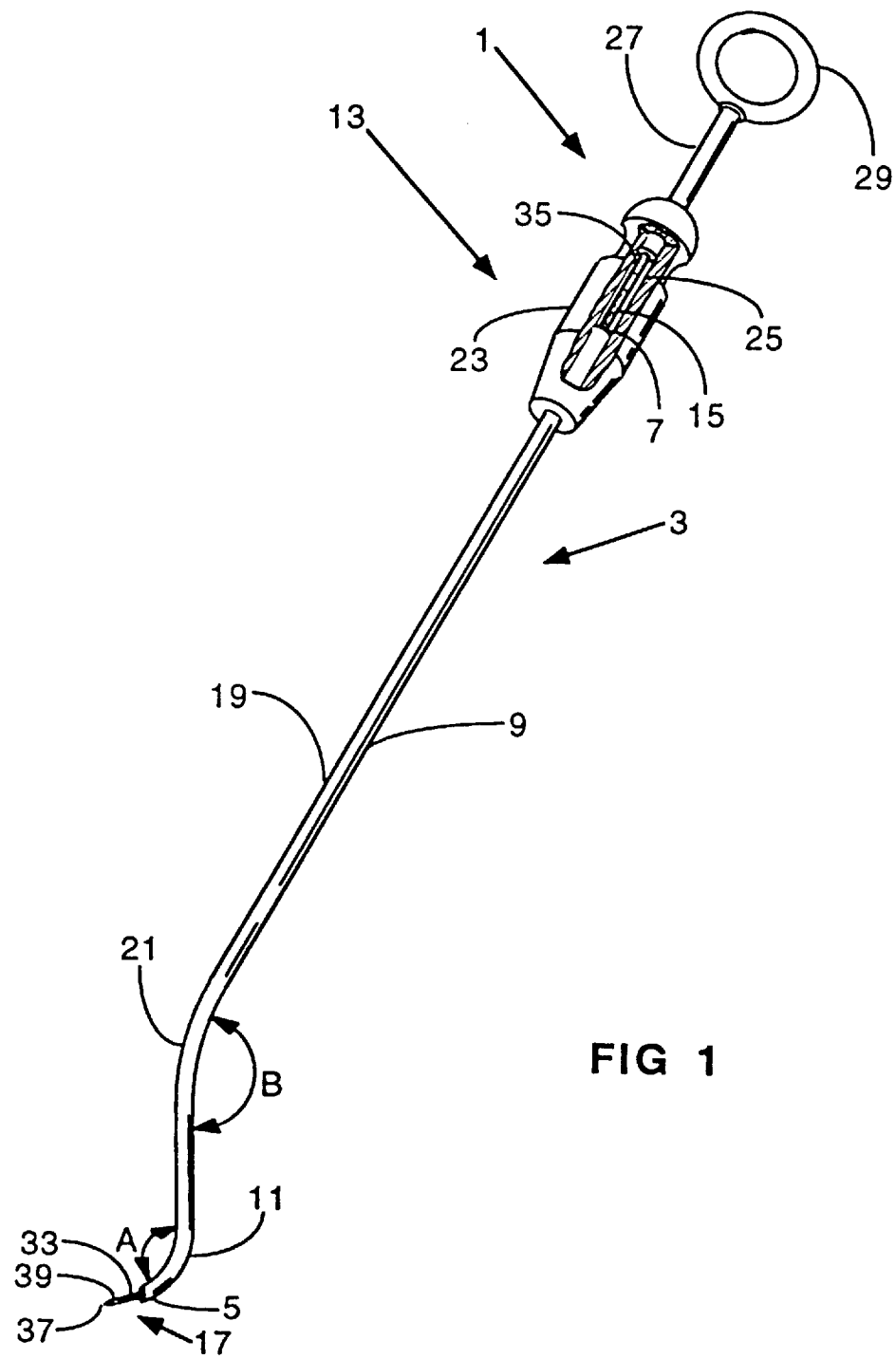
FIG. 1 is a perspective view of a suturing instrument of the present invention.
Figure 2:
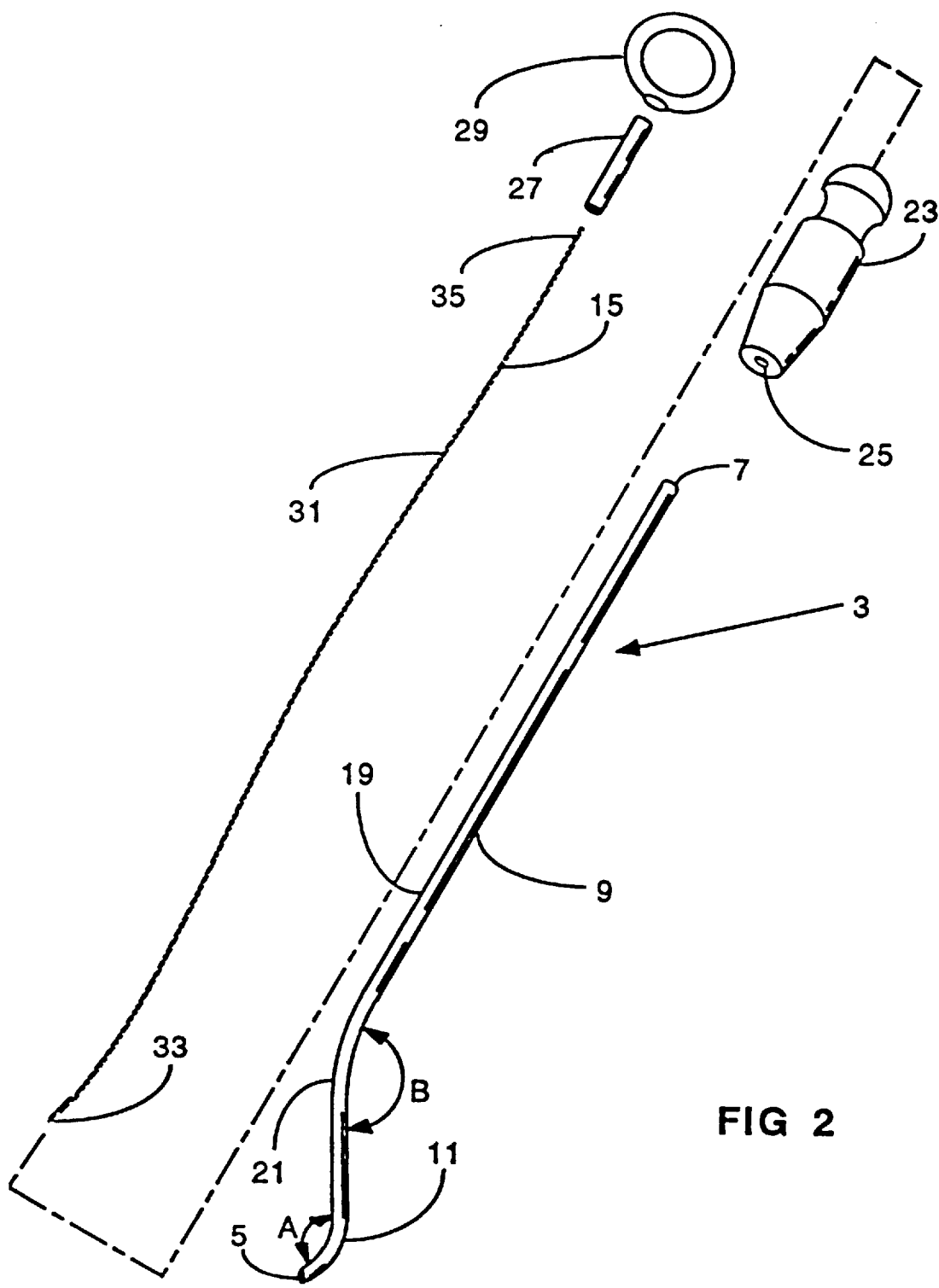
FIG. 2 is an exploded view of the instrument of FIG. 1.

Referring now to the drawings, and first more particularly to FIGS. 1 and 2, a suturing instrument of the present invention is indicated in its entirety by the reference numeral 1. The instrument 1 may be used in any suturing procedures, but it is especially useful in radical prostatectomy procedures to ligate the distal end of the dorsal vein complex D (FIG. 5) before the veins are severed.

As shown in FIG. 1, the instrument 1 comprises a substantially rigid guide tube 3 having opposite open ends 5, 7 which are distal and proximal relative to a person using the instrument. The guide tube 3 has a shank portion 9 and a distal end portion 11 extending generally laterally with respect to the shank portion. A handle assembly, indicated generally as 13, is fixedly attached to the shank portion 9 of the guide tube 3 generally adjacent the proximal end 7 of the guide tube. The instrument 1 also includes a stiff but flexible shaft 15 which extends through the guide tube 3, and a suture thread holder, indicated generally as 17, adjacent the distal end of the shaft.

The guide tube 3 is preferably, but not necessarily, formed from a single piece of bent metal tube. The guide tube 3 has a substantially straight shank portion 9 and a distal end portion 11 extending generally laterally from the shank portion at an angle A not substantially less than 90 degrees. This angle is preferably 90–135 degrees and more preferably about 90 degrees. The shank portion 9 has a long substantially straight main section 19, and a distal section 21 which is bent from the straight section at an angle B preferably in the range of 90–180 degrees, and more preferably about 150 degrees. When the suturing instrument 1 is in use, the main and distal sections 19, 21 of the shank portion 9 of the guide tube 3 lie in the same vertical plane.

As illustrated best in FIGS. 1 and 2, the handle assembly 13 comprises a generally cylindric handle 23, preferably of metal, having a central bore 25 therethrough for receiving the proximal end 7 of the guide tube 3 which is fixedly affixed to the handle in any suitable fashion. The assembly 13 also includes a rigid (e.g., metal) sleeve 27 axially slidable within the handle bore 25 and projecting in a proximal direction from the bore, and grasping means in the form of a finger loop 29 (e.g., a metal ring) attached to the proximal end of the sleeve. The sleeve 27 is axially slidable in the bore 25 relative to the handle 23 between the positions shown in FIGS. 3 and 4. The outer surface of the handle 23 is contoured, knurled and otherwise configured to provide a suitably comfortable and secure grip on the instrument 1.

The shaft 15 preferably comprises a stiff but flexible and resilient rod which is substantially straight when unrestrained. The preferred shaft material is plastic (e.g., nylon 3/3) to keep costs sufficiently low to allow for disposal of the shaft 15 after a single use. However, other materials may also be suitable. In the embodiment shown, the overall length of the shaft 15 is greater than the length of the guide tube 3, the shaft having a middle part 31 inside the guide tube, a distal end part 33 which is adapted to extend distally through and beyond the distal (lower) open end 5 of the guide tube, and a proximal end part 35 which extends proximally through the proximal (upper) open end 7 of the guide tube, through the central bore 25 in the handle 23 and into the sleeve 27 where it is secured in fixed position relative to the sleeve and to the finger loop 29. The shaft 15 may be secured to the sleeve 27 and/or loop 29 in any suitable fashion. The distal end part 33 of the shaft 15 has a tapered tip 37 sufficiently sharp to penetrate tissue during a suturing procedure (to be described later).

The suture thread holder 17 is located immediately adjacent the tip 37 of the distal end part 33 of the shaft 15. The holder 17 comprises an opening 39 in the form of an eye in the shaft 15, although it will be understood that other types of openings (e.g., a slot) or other suture thread holding mechanism could be used without departing from the scope of this invention. The opening 39 is sized to receive a suture thread 41 therethrough, much like the eye of a sewing needle (see FIG. 6).

While the shaft 15 shown in the drawings is fabricated from a single piece of flexibly resilient rod, it will be understood that the shaft may be formed in multiple pieces. For example, the shaft 15 could comprise a length of metal cable surrounded by plastic sheathing, and a short tapered metal tube secured to the distal end of the cable having an opening thereon constituting the suture thread holder. Other configurations are also possible.

The shaft 15 is manually movable relative to the guide tube 3 by pushing and pulling on the finger loop 29 attached to the sleeve 27 which is slidable in the handle bore 25. In this manner the distal end part 33 of the shaft 15 may be moved from a retracted position (FIG. 3) in which the suture thread holder 17 is generally adjacent the open distal end 5 of the guide tube 3, to an extended position (FIG. 4) in which the suture thread holder is farther away from the distal end of the guide tube and farther away from the shank portion 9 of the guide tube. (The tip 37 of the shaft 15 may or may not be fully retracted inside the guide tube 3 when the shaft is in its stated "retracted" position.) The distal end portion 11 of the guide tube 3 is configured (e.g., bent) to guide the distal end part 33 of the shaft 15 and the suture thread holder 17 thereon along a substantially straight path extending along the axis designated AX in FIGS. 3, 4 and 6. This axis generally corresponds to the axis of the distal end portion 11 of the guide tube 3 which, as previously noted, extends generally laterally at an angle of not substantially less than ninety degrees with respect to the shank portion 9 of the guide tube, the more preferable angle being about 90 degrees. It is desirable that the suture thread holder 17 move along a straight path so that its movement and position during a suturing operation are accurately predictable.

The distal end of the sleeve 27 of the handle assembly 13 is engageable with the proximal end 7 of the guide tube 3 to limit extension of the shaft 15 in a distal direction relative to the guide tube 3.

The handle assembly 13 of the present invention is designed to prevent buckling of the proximal end part 35 of the shaft 15 as the shaft is pushed to move the distal end part 33 of the shaft (and the suture thread holder 17 thereon) to its extended position shown in FIG. 4. To this end, the sleeve 27 preferably has an inside diameter only slightly greater than the diameter of the shaft 15, and the bore 25 in the handle 23 has a diameter only slightly greater than the diameter of the shaft, the shaft thus being constrained against buckling as it is pushed forward. It is contemplated that the sleeve 27 may not be needed if the shaft 15 is sufficiently stiff to resist buckling without reinforcement, in which case the proximal end part 35 of the shaft may be bent to form an integral finger loop, thereby also eliminating the need for a separate metal ring. The aforementioned grasping means may take forms other than an integral finger loop 29 or a metal ring affixed to the sleeve 27.

For purposes of illustration only, the guide tube 3 may be formed from a length of stainless steel tubing having an inside diameter of 0.10 in. and an outside diameter of 0.13 in. The main and distal sections 19, 21 of the shank portion 9 of the guide tube 3 may have lengths of 8.0 in. and 2.5 in., respectively; and the distal end portion 33 of the guide tube 3 may have a length of 0.75 in. The flexible shaft 15 may have a diameter of 0.09 in. and an overall length of 16.0 in. When the shaft 15 is in its extended position, the distance between the distal end 5 opening of the guide tube 3 and the tip 37 of the shaft is preferably in the range of 1.0 in. to 1.5 in., and more preferably about 1.25 in.

The following is a description of how the instrument 1 is used in a radical prostatectomy. It will be understood that the instrument 1 can be used in other suturing procedures.

Figure 7:
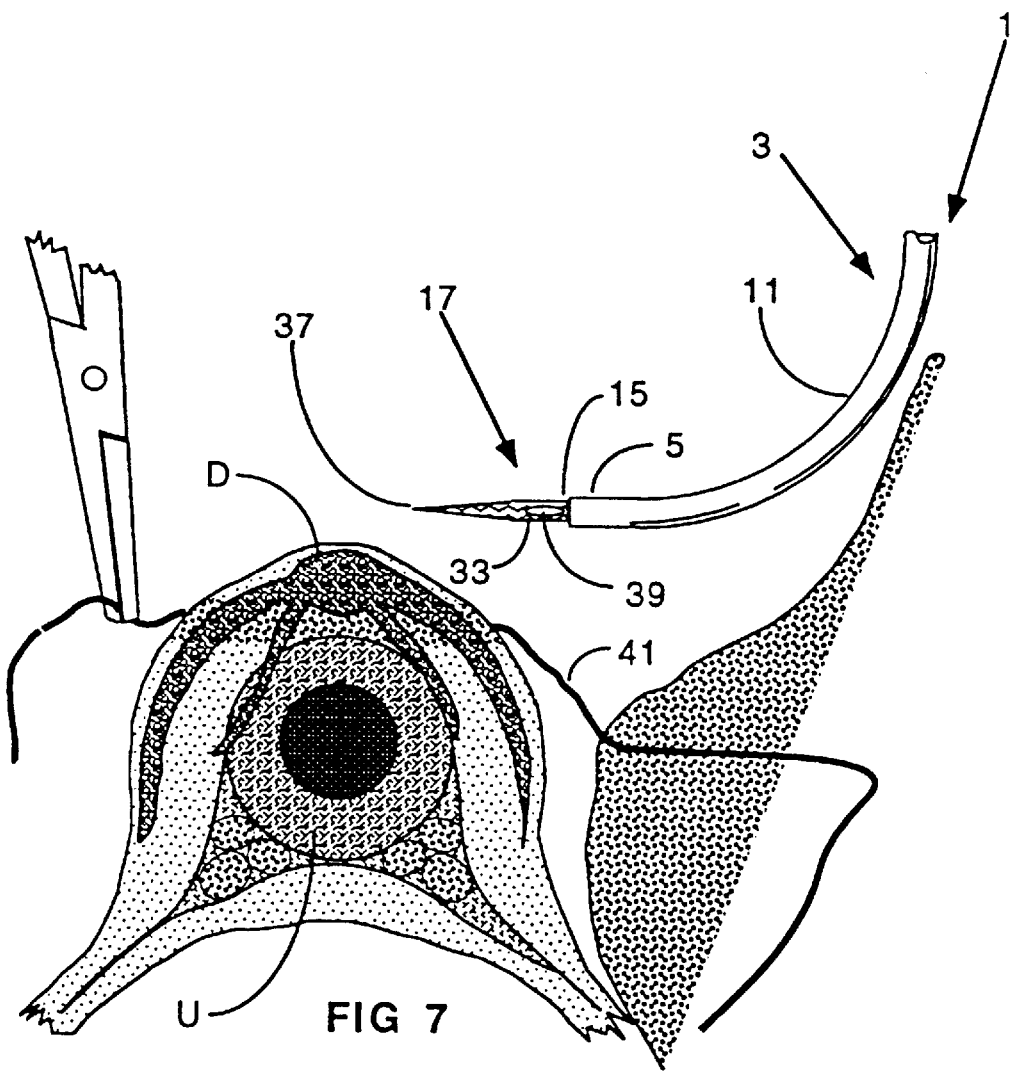

With reference to FIGS. 5–7, after the appropriate incision has been made to expose the urethra U, the prostate and dorsal vein complex D (the distal end of which is difficult to see and access because it underlies the pubic bone), the instrument 1 carrying a suture thread 41 in the opening 39 of the holder 17 is placed in a position in which the main section 19 of the shank portion 9 of the guide tube 3 extends to a position adjacent the pubic bone, the distal section 21 of the shank portion 9 extends down and under the pubic bone, and the distal end portion 11 of the guide tube 3 extends laterally toward the avascular plane AP which underlies the distal end of the dorsal vein complex D (see FIG. 5). As thus positioned, the main and distal sections 19, 21 of the shank portion 9 of the guide tube 3 lie in the same vertical plane; the distal end portion 11 of the guide tube 3 extends laterally relative to this plane; and the shaft 15 is in its retracted position. While gripping the handle 23 with one hand, and using the other hand to push the finger loop 29, sleeve 27 and shaft 15 in a distal direction relative to the handle and the guide tube 3, the distal end part 33 of the shaft 15 is moved to its extended position along a straight line path through the avascular plane AP, under the pubic bone PB, to a position beyond the distal end of the dorsal vein complex D (FIG. 6). During this movement, the tapered tip 37 of the shaft 15 penetrates tissue, and the suture thread holder 17 carries the suture thread 41 to a location where it may be grasped by the surgeon and then used to ligate the distal end of the dorsal vein complex D (FIG. 7). The shaft 15 is retracted either before or after the ligation is completed by pulling on the finger loop 29. The process may be repeated to ligate the proximal end of the dorsal vein complex D. The dorsal vein is severed after this procedure is complete.

Figure 8:
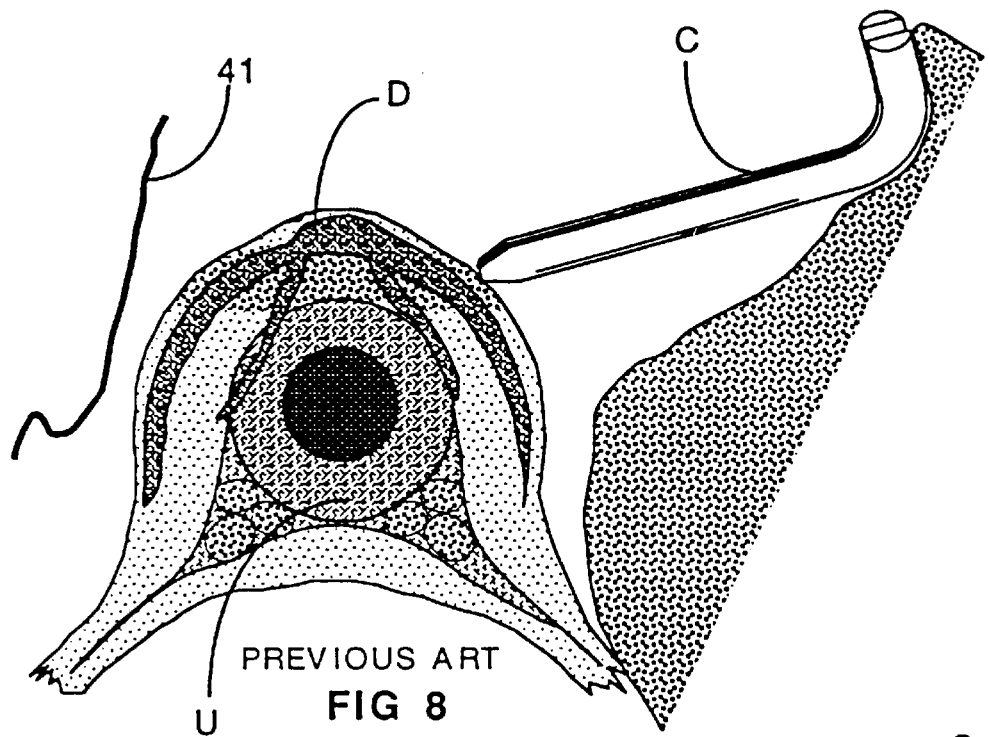
FIGS. 8–10 illustrate the use of conventional instrument in the same procedure.
Figure 9:
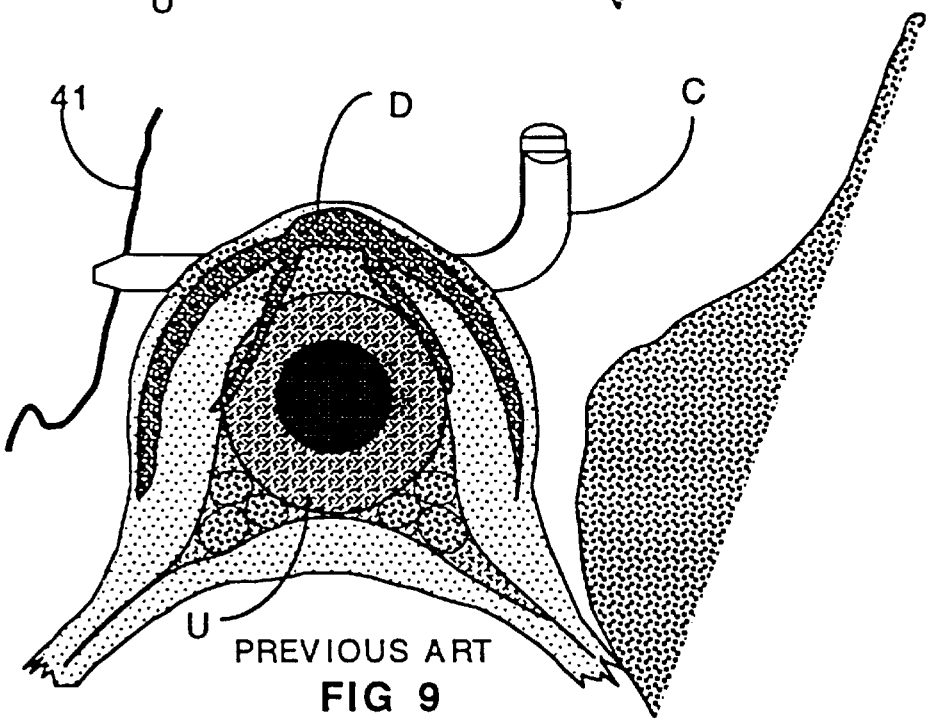
Figure 10:
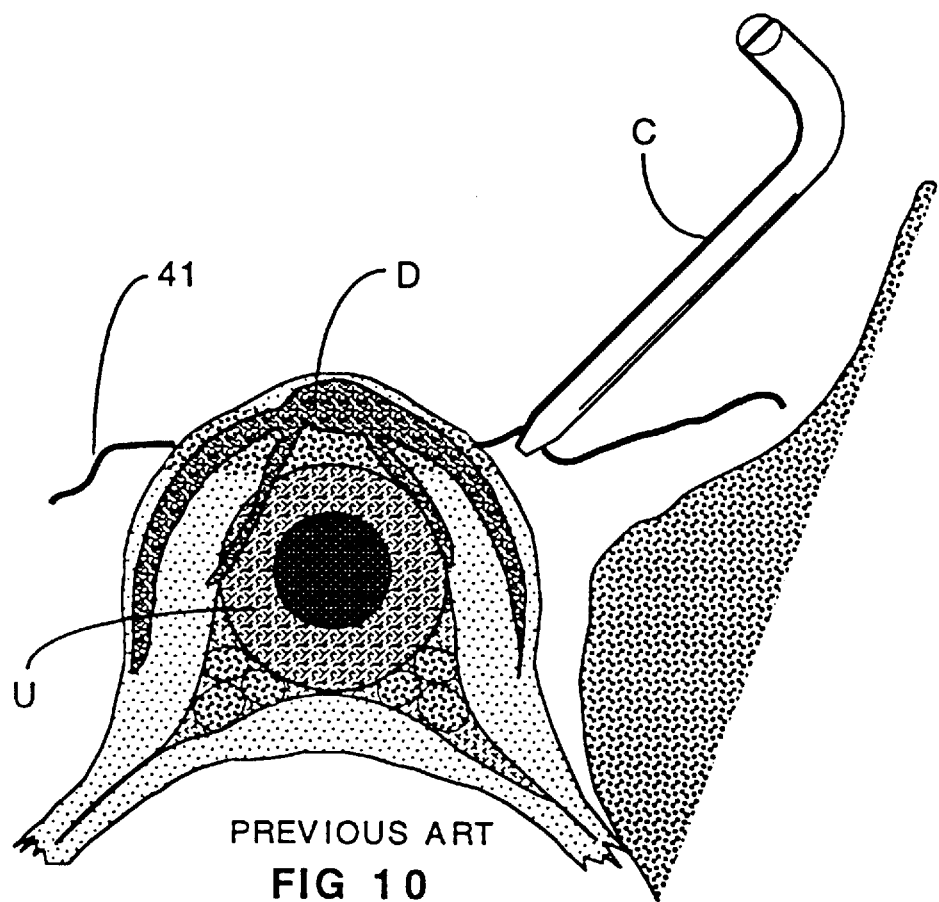

It will be apparent from the foregoing that the instrument 1 of the present invention will facilitate the suturing procedure. This is best demonstrated by comparing the process described above using the instrument 1 of the present invention to a radical prostatectomy carried out using a conventional instrument and procedure. FIGS. 8–10 illustrate such a procedure using a prior art right angle clamp C. In this procedure the clamp C is positioned as shown in FIG. 8 and bluntly and blindly pushed through the avascular plane of the dorsal vein complex D. A suture thread 41 is then placed in the jaws of the clamp C (FIG. 9) and pulled back to the position shown in FIG. 10, whereupon the dorsal vein complex D may be tied off. This technique is more traumatic and less controlled, and increases the risk of tearing the fragile dorsal vein complex D.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A suturing instrument for use in a suturing procedure, comprising
    a substantially rigid guide tube having opposite open ends which are distal and proximal relative to a person using the instrument, said guide tube having a shank portion and a distal end portion extending generally laterally with respect to the shank portion,
    a handle on the shank portion of the guide tube generally adjacent the proximal end of the guide tube,
    a stiff but flexible shaft inside the guide tube having a distal end part movable distally relative to the guide tube to extend through and beyond the open distal end of the guide tube, and
    a suture thread holder on the distal end part of the shaft,
    said shaft being manually movable longitudinally relative to the guide tube to move the distal end part of the shaft from a retracted position in which the suture thread holder is generally adjacent the open distal end of the guide tube, to an extended position in which the suture thread holder is farther away from the distal end of the guide tube and farther away from the shank portion of the guide tube, the distal end portion of the guide tube being configured to guide the distal end part of the shaft and the suture thread holder thereon along a substantially straight path extending generally laterally at an angle of not less than about ninety degrees with respect to the shank portion of the guide tube.

2. A suturing instrument as set forth in claim 1 wherein said suture thread holder comprises an opening formed in the distal end part of the shaft.

3. A suturing instrument as set forth in claim 3 wherein said opening is an eye.

4. A suturing instrument as set forth in claim 1 wherein the distal end portion of the guide tube extends at an angle of 90–135 degrees relative to the shank portion of the guide tube.

5. A suturing instrument for use in a suturing procedure, comprising:
    a substantially rigid guide tube having opposite open ends which are distal and proximal relative to a person using the instrument, said guide tube having a shank portion and a distal end portion extending generally laterally with respect to the shank portion,
    a handle on the shank portion of the guide tube generally adjacent the proximal end of the guide tube,
    a stiff but flexible shaft inside the guide tube having a distal end part movable distally relative to the guide tube to extend through and beyond the open distal end of the guide tube, and
    a suture thread holder on the distal end part of the shaft,
    said shaft being manually movable relative to the guide tube the distal end part of the shaft having a sharp tip for penetrating tissue, to move the distal end part of the shaft from a retracted position in which the suture thread holder is generally adjacent the open distal end of the guide tube, to an extended position in which the suture thread holder is farther away from the distal end of the guide tube and farther away from the shank portion of the guide tube, the distal end portion of the guide tube being configured to guide the distal end part of the shaft and the suture thread holder thereon along a substantially straight path extending generally laterally at an angle of not less than about ninety degrees with respect to the shank portion of the guide tube.

6. A suturing instrument for use in a suturing procedure, comprising:
    a substantially rigid guide tube having opposite open ends which are distal and proximal relative to a person using the instrument, said guide tube having a shank portion and a distal end portion extending generally laterally with respect to the shank portion,
    a handle on the shank portion of the guide tube generally adjacent the proximal end of the guide tube,
    a stiff but flexible shaft inside the guide tube having a distal end part movable distally relative to the guide tube to extend through and beyond the open distal end of the guide tube, said shaft being resilient and having a middle part disposed inside the guide tube, said middle part and distal end part of the shaft being substantially straight and collinear when the shaft is unrestrained, and
    a suture thread holder on the distal end part of the shaft, the suture thread holder comprising an opening formed in the distal end part of the shaft,
    said shaft being manually movable relative to the guide tube to move the distal end part of the shaft from a retracted position in which the suture thread holder is generally adjacent the open distal end of the guide tube, to an extended position in which the suture thread holder is farther away from the distal end of the guide tube and farther away from the shank portion of the guide tube, the distal end portion of the guide tube being configured to guide the distal end part of the shaft and the suture thread holder thereon along a substantially straight path extending generally laterally at an angle of not substantially less than ninety degrees with respect to the shank portion of the guide tube.

7. A suturing instrument as set forth in claim 3 wherein the shaft has a length greater than that of the guide tube, said shaft having a proximal end part extending proximally through and beyond the open proximal end of the guide tube, and grasping means adjacent the proximal end of the shaft adapted to be grasped by one hand while holding the handle with the other hand, said grasping means being adapted to be pushed and pulled to move the shaft relative to the guide tube in distal and proximal directions.

8. A suturing instrument as set forth in claim 6 wherein said grasping means comprises a finger loop at the proximal end of the shaft.

9. A suturing instrument as set forth in claim 6 wherein the shaft is a one piece plastic shaft.

10. A suturing instrument as set forth in claim 6 wherein said handle has a central bore therethrough, the proximal end of the guide tube being affixed within said bore, and said instrument further comprising a rigid sleeve around the proximal end part of the shaft to prevent buckling of the proximal end part of the shaft as said grasping means is pushed in a distal direction to move the distal end part of the shaft to its extended position, said sleeve being slidable within said bore toward and away from said guide tube.

11. A suturing instrument as set forth in claim 3 wherein said guide tube is formed from a single piece of bent tubular metal.

12. A suturing instrument as set forth in claim 10 wherein the distal end portion of the guide tube extends at an angle of 90–135 degrees relative to the shank portion of the guide tube.

13. A suturing instrument as set forth in claim 11 adapted for use in a radical prostatectomy, the shank portion of the guide tube having a straight main section and a distal section bent at a second angle relative to the main section whereby when the instrument is held in use during the procedure the main section of the shank portion of the guide tube extends to a position adjacent the pubic bone, the distal section of the shank portion extends down and under the pubic bone, and the distal end portion of the guide tube extends laterally toward the avascular plane under the dorsal vein complex, so that upon movement of the shaft to its extended position, a suture thread held by the suture holder is carried through the avascular plane below the dorsal vein complex to a location beyond the dorsal vein complex.

14. A suturing instrument as set forth in claim 13 wherein said second angle is 90–180 degrees.

15. A suturing instrument as set forth in claim 14 wherein said second angle is about 150 degrees.

16. A suturing instrument for use in a radical prostatectomy, comprising:

a substantially rigid guide tube having opposite open ends which are distal and proximal relative to a person using the instrument, said guide tube having a shank portion and a distal end portion extending generally laterally with respect to the shank portion, a handle on the shank portion of the guide tube generally adjacent the proximal end of the guide tube, a stiff but flexible shaft inside the guide tube having a distal end part movable distally relative to the guide tube to extend through and beyond the open distal end of the guide tube, and a suture thread holder on the distal end part of the shaft, said shaft being manually movable relative to the guide tube to move the distal end part of the shaft from a retracted position in which the suture thread holder is generally adjacent the open distal end of the guide tube, to an extended position in which the suture thread holder is farther away from the distal end of the guide tube and farther away from the shank portion of the guide tube, the distal end portion of the guide tube being configured to guide the distal end part of the shaft and the suture thread holder thereon along a substantially straight path extending generally laterally at an angle of not substantially less than ninety degrees with respect to the shank portion of the guide tube, the shank portion of the guide tube having a straight main section and a distal section bent at a second angle relative to the main section whereby when the instrument is held in use during the procedure the main section of the shank portion of the guide tube extends to a position adjacent the pubic bone, the distal section of the shank portion extends down and under the pubic bone, and the distal end portion of the guide tube extends laterally toward the avascular plane under the dorsal vein complex, so that upon movement of the shaft to its extended position, a suture thread held by the suture holder is carried through the avascular plane below the dorsal vein complex to a location beyond the dorsal vein complex.

17. A suturing instrument as set forth in claim 16 wherein said second angle is 90–180 degrees.

18. A suturing instrument as set forth in claim 17 wherein said second angle is about 150 degrees.

* * * * *